US007492388B2

(12) United States Patent
Odlivak et al.

(10) Patent No.: US 7,492,388 B2
(45) Date of Patent: Feb. 17, 2009

(54) SYSTEM AND METHOD FOR AUTOMATIC PROCESSING OF ENDOSCOPIC IMAGES

(75) Inventors: Andrew Odlivak, Oakdale, NY (US); Philip Pearson, Sea Cliff, NY (US); Marc Shapiro, Dix Hills, NY (US); Deepak Agarwal, Hicksville, NY (US); Aaron Divinsky, Sayville, NY (US); Peter B. Cotton, Mt. Pleasant, SC (US)

(73) Assignee: Olympus Corporation, Tokyo (JP)

( * ) Notice: Subject to any disclaimer, the term of this patent is extended or adjusted under 35 U.S.C. 154(b) by 962 days.

(21) Appl. No.: 10/846,253

(22) Filed: May 14, 2004
(Under 37 CFR 1.47)

(65) Prior Publication Data
US 2005/0073578 A1    Apr. 7, 2005

Related U.S. Application Data

(60) Provisional application No. 60/471,349, filed on May 16, 2003.

(51) Int. Cl.
*A62B 1/04* (2006.01)
*A61B 1/00* (2006.01)
(52) U.S. Cl. .......................................... 348/65; 600/118
(58) Field of Classification Search ............... 348/65, 348/71, 74; 600/118, 407, 427
See application file for complete search history.

(56) References Cited

U.S. PATENT DOCUMENTS 4,727,418 A * 2/1988 Kato et al. ................... 348/74
5,031,036 A * 7/1991 Kikuchi et al. .............. 348/71
5,305,098 A * 4/1994 Matsunaka et al. ........... 348/65
5,740,801 A * 4/1998 Branson ..................... 600/407
5,871,439 A * 2/1999 Takahashi et al. ........... 600/118
6,950,691 B2 * 9/2005 Uchikubo ................... 600/427

FOREIGN PATENT DOCUMENTS

WO    WO 00/08585    2/2000

OTHER PUBLICATIONS

"Introducing EndoWorks®", ENDOWORKS7 ©2003 Olympus America Inc.

(Continued)

*Primary Examiner*—Gims S Philippe
(74) *Attorney, Agent, or Firm*—Scully, Scott, Murphy & Presser, P.C.

(57) ABSTRACT

A system and method for enabling the automatic setting of a mask for displaying live endoscopic images on a monitor device. An imaging node processor selects a pre-determined mask setting based on an automatically detected solid state imager (CCD) type when connected to the video processor, and a selected magnifying ratio. Based on this information, a mask pattern is automatically generated in a main memory. A merge function enables the mask to be displayed with cutout portions where information including, live or frozen image, thumbnail image associated with a static image capture, and patient demographic information is displayed. The user may select the frame coordinate locations corresponding to the corners of the live viewable area, captured image display and other system and demographic information to be displayed. Further, while the system is configured to include pre-defined masks, users are additionally able to create additional masks or modify the system-defined masks. The user can associate a mask to one or more scopes or video chip (imager) types.

26 Claims, 7 Drawing Sheets

OTHER PUBLICATIONS

Nelson, et al., "Computerized Endoscopic Medical Record Systems", Gastrointestinal Endoscopy, vol. 51, No. 6, Jun. 2000, pp. 793-796, XP002404675.

General Medical Applications: "gCare Features", Internet Citation, (online), Nov. 4, 1999, XP002404676, URL:http://web/archive.org/web/19991104023648/http://www.gmedcorp.com/Products/gcare_features.htm>, last retrieved on Oct. 26, 2006.

Pentax Medical: "Pentax—Computer Products: endoPro, IMS, Doc-U-Scribe", Internet Citation, (online) Oct. 2000, XP002404677, URL:http://web.rchive.org/web/20001011154939/www.pentamedical.com/computers.asp>, last retrieved on Oct. 26, 2006.

Dayhoff, et al., "Providing a Complete Online Multimedia Patient Record", Proceedings of the AMIA '99 Annual Symposium, (online), Nov. 1999, XP002404678, URL: http://www.amia.org/pubs/symposia/D0005623.PDF>, last retrieved on Oct. 26, 1999.

* cited by examiner

RGB MONITOR AND PROCESSOR

IMAGING WORKSTATION

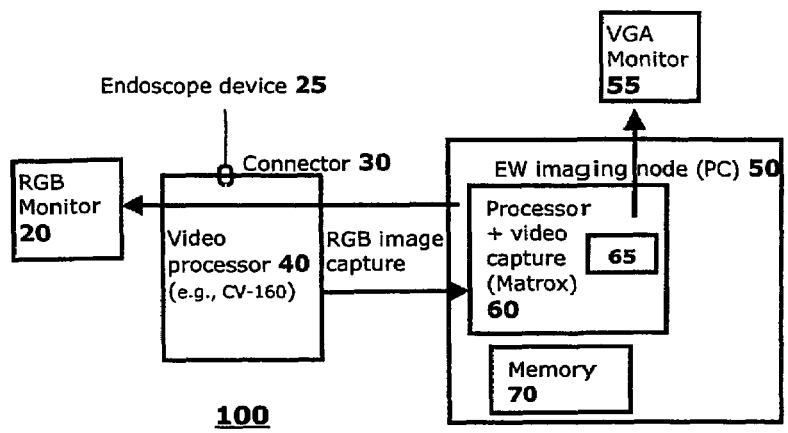
Figure 3
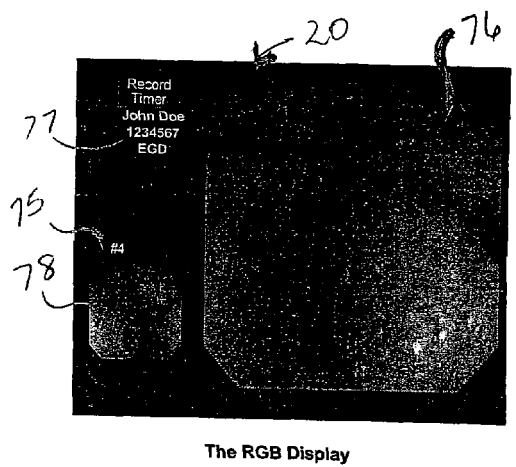
The RGB Display
Fig 6
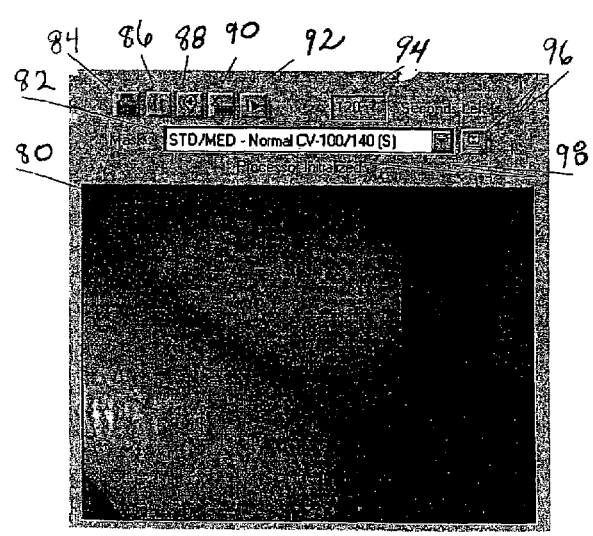
Fig 7  The ActiveX Control and VGA Display

SYSTEM AND METHOD FOR AUTOMATIC PROCESSING OF ENDOSCOPIC IMAGES

CROSS REFERENCE TO RELATED APPLICATION

This application claims the benefit of U.S. Provisional Patent Application Ser. No. 60/471,349 filed May 16, 2003 and incorporated by reference as if fully set forth herein. This application further relates to commonly-owned, co-pending U.S. patent application Ser. Nos. 10/846,255, 10/846,254 and 10/846,245 incorporated by reference herein.

BACKGROUND OF THE INVENTION

1. Field of the Invention

The present invention relates generally to imaging systems and workstations for medical applications, and particularly the generation, processing and displaying of endoscopic images on a display device, e.g., a television monitor.

2. Discussion of the Prior Art

There currently exists a clinical information management system known as Endoworks (hereinafter "EW system" manufactured by Olympus Corporation) that provides functionality for automating the endoscopy lab by managing patient examination data at different phases of patient care.

Particularly, the EW system, designed for the practice of endoscopy, is a comprehensive, real-time, interactive clinical information management system with integrated reporting features, that manages and organizes clinical information, endoscopic images and related patient data, at various levels of detail, for creating efficiencies and facilitating functions performed by users of endoscopic equipment, e.g., physicians, nurses, clinicians, etc.

Integral to the performance of an endoscopy procedure is the real-time presentation of endoscopic images and related examination data (e.g., patient ID, practitioner information, endoscope ID type). Typically, endoscopic image signals of an examined subject are obtained from a solid state (e.g., charge coupled devices, CCD) imager device provided with the scope device. The generated output scope image signals are input to a video processor device where the scope image signals are converted to a video signal, e.g., according to NTSC, PAL or like color image display formats, for display and real-time viewing on an RGB display device 20, e.g., a television monitor.

It is understood that, in practice, an endoscope device being used to perform a particular procedure, (e.g., gastrointestinal, pulmonary, etc.) will vary in size, and depending upon the procedure being performed, certain scopes types will have certain solid state imager (CCD) sizes. Correspondingly, the size of a resulting image displayed will vary dependent upon the type of scope being implement. Further, during the course of an examination, to aid in image viewing, the practitioner may initiate the magnification of an image. In the EW7, functionality is provided with the video processor device to enable to enable the practitioner to select one from among a plurality of magnification ratios. For example, as shown in FIG. 1(a), a video processor device will output signals resulting in a displayed image field 10 on TV monitor screen 20 for a particular CCD type. Upon selection of a particular magnification ratio for that scope CCD type, for example corresponding to medium, semi-full height or full height, the video processor device will be able to display either of the image fields 10a, 10b, 10c, respectively, as illustrated in FIGS. 1(b)-1(d), respectively.

Further, as shown in FIGS. 1(a)-1(d) an image mask 11, 11a, 11b, 11c, and 11d is generated that defines the borders of the real-time image seen both on the RGB and VGA monitors, plus any other informational cutouts. Particularly, the mask is implemented to present the pertinent real-image portion generated by the particular endoscope device implemented on the screen in a specified area and prevent non-pertinent image portions from being displayed, and thus, conserve display monitor screen space other graphic information that may be simultaneously displayed. That is, besides defining the displayed image area, the mask is implemented so that pertinent endoscopic procedure information 25, such as patient information, attending physician and endoscope ID type, etc. may be displayed on the monitor screen 20 in a manner so as to avoid overlap with the displayed image. The use of the mask in the EW system is particularly important, for instance, when a selected image is magnified, for example, as shown by images 10, 10a, 10b, 10c, and 10d in FIGS. 1(a)-1(d) for the display on both monitors (RGB And VGA) implemented in the EW7 system.

Currently, any mask setting used for the real-time display of images on the RGB display is conducted manually prior to the actual performance of the endoscopic procedure. During the course of an examination, it is further necessary for the practitioner to reconfigure a mask setting when a different magnification ratio is selected.

It would thus be highly desirable to provide a system that will automatically configure the mask setting for the displayed endoscopic image field, thereby obviating the need for the healthcare practitioner to manually configure the mask setting upon use of an endoscope having a different endoscope imager (CCD) size, or when a different magnification ratio is selected.

SUMMARY OF THE INVENTION

Accordingly, it is an object of the present invention to provide a novel system and method for generating, processing and displaying endoscopic images on a monitor device.

Further it is an object of the invention to provide an image display mask function for a real-time endoscopic image display system that automatically selects an appropriate video mask for real-time image and captured still/motion image display generation based on a particular endoscope device being utilized by the healthcare practitioner.

Further it is an object of the invention to provide an image display mask function for a real-time endoscopic image display system that automatically selects an appropriate video mask for real-time image and captured still/motion image display generation based on a particular endoscope device being used and a particular image magnification ratio selected for image display by the healthcare practitioner.

According to the preferred aspects of the invention there is provided an automatic mask setting system for an endoscopic system comprising an imaging node adapted to capture digital images during the course of an endoscopic examination, and store the images in a memory, and, a video processor adapted for receiving images during the course of an endoscopic examination and for processing the images suitable for display on a monitor. The system comprises: a means for discriminating use of a particular video processor device receiving the images of an organ examined during the endoscopic examination; a means for automatically receiving information regarding the imager device; a means for configuring a mask setting in a memory according to the endoscope type and imager device information, and a display means for displaying live video or captured images from said endoscope in a pre-defined portion of a display screen on the display means as specified by the mask setting.

Advantageously, the image display automask feature is implemented in a comprehensive, browser-based, clinical information management system that includes an Image Management function enabling a user to annotate, label, import, export, and enhance the quality of images, including the ability to manage, record, and export live video clips.

BRIEF DESCRIPTION OF THE DRAWINGS

The objects, features and advantages of the present invention will become apparent to one skilled in the art, in view of the following detailed description taken in combination with the attached drawings, in which:

FIG. 3 is a block diagram depicting the endoscopy lab 100 for generating, processing and displaying of real-time endoscopic images;

FIG. 6 illustrates an exemplary the RGB monitor display 75 comprising several mask "cutouts";

FIG. 7 illustrates an exemplary the ActiveX control and VGA display generated according to the present invention;

DETAILED DESCRIPTION OF THE PREFERRED EMBODIMENT

Figure 2:
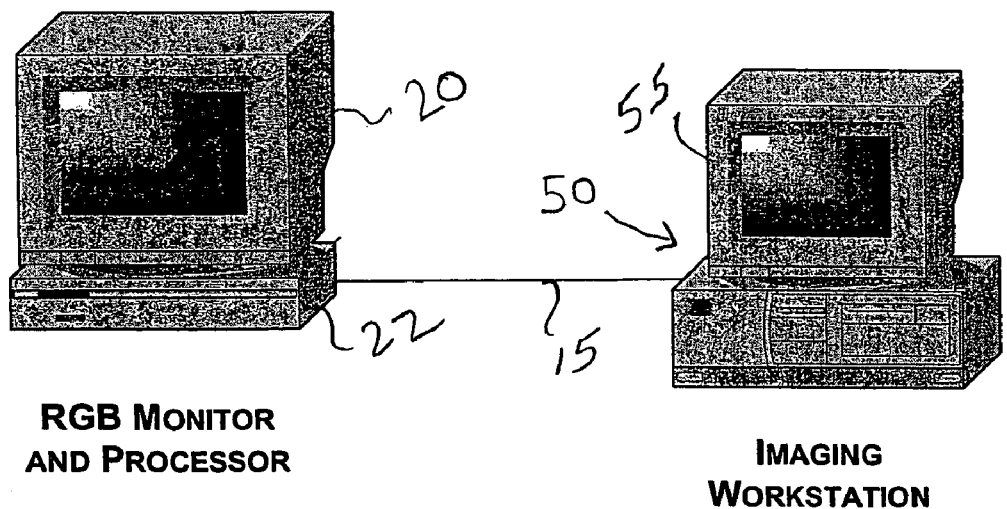
FIG. 2 illustrates the communication between a video processor device including a first display device for displaying live endoscopic images, and, an imaging workstation comprising a second display device according to an aspect of the invention.

In a particular implementation of the EW7, as shown in FIG. 2, video image signals output of a video processor device 22 receiving live endoscopic images are communicated via interface 15 to an EW imaging workstation 50 (imaging "node") where the video image signals are captured and further displayed in a separate monitor, e.g., imaging workstation display such as a VGA graphics monitor 55, which may be a scaled version of the RGB monitor with aspect ratio preserved. As will be explained in greater detail herein, upon initiation by the practitioner, the video image signals may be captured, processed (digitized) and stored in a memory at the imaging node. Not only are still images available for capture, but live moving image clips are further capable of being captured and stored in an EW system memory or server database. The EW system imaging node particularly implements image management functionality enabling a user to annotate, label, import, export, and enhance the quality of images, including the ability to manage, record, store and export live video clips. It is understood that every image/image clip captured are associated (i.e., linked) with the particular patient and capable of being accessed according to entry of a key, e.g., the patient's name.

FIG. 3 is a block diagram depicting the endoscopy lab 100 for generating, processing and displaying of real-time endoscopic images. As shown in FIG. 3, the system comprises an endoscope device 25 connected via a connector device 30 to the video processor device 40, for example, an Olympus CV-160 device. As mentioned the endoscopic device includes a solid state CCD imager for generating real-time frame image signals, e.g., simultaneously generated RGB signals, which are processed by the video processor device to generate real-time video signals of the image for display on an RGB monitor 20. As shown the video processor is further connected via communications interface 15, to an imaging node 50, e.g., a personal computer (PC) or workstation 50, including a processor 60, a video frame capture board for capturing the real-time video image and digitizing the image, and, a memory 70 device for storing the captured, digitized image for storage in memory 70, and including a video display driver element for further displaying a scaled version of the image, for example, on a second monitor, e.g., VGA monitor device 55. In one embodiment, the processor implemented at the imaging node 50 includes a Matrox Orion (available from Matrox Electronic Systems Ltd., Quebec Canada) which is a frame grabber board that captures standard analog composite and Y/C video in NTSC/PAL formats from the video processor 40 and includes analog to digital converters for capturing the component RGB in the NTSC/PAL video formats. The captured field are stored in the main memory 70 of the imaging node. A graphics controller (not shown) provided with the Matrox board is provided for handling VGA display output and includes a graphics overlay and video scaling.

More particularly, the image capture board is further capable of capturing images from any of the following video input signal sources: Standard NTSC (or optional PAL) composite, component RGB or Y/C video (optional depending on model). The board is capable of digitizing images, for example, at a resolution of 768 pixels by 576 lines in size (from a full PAL frame; a full NTSC frame is 640 pixels by 480 lines), and at a color depth of 8 bits for each of the RGB components. There is sufficient capability to capture full screen images. The board is further able to provide output of both RGB and NTSC composite interlaced video signal for display on the interlaced monitors supported by this workstation; however, PAL-compatible output are also supported. As described in greater detail herein, to support the overlay of graphics information (including text such as patient information data) on the video input signal, the capture board 60 is capable of masking out any desired portion of the video input signal. The image capture board additionally permits the simultaneous connection of multiple video input signal types (such as RGB and composite) and be able to switch between them under software control.

Figure 4:
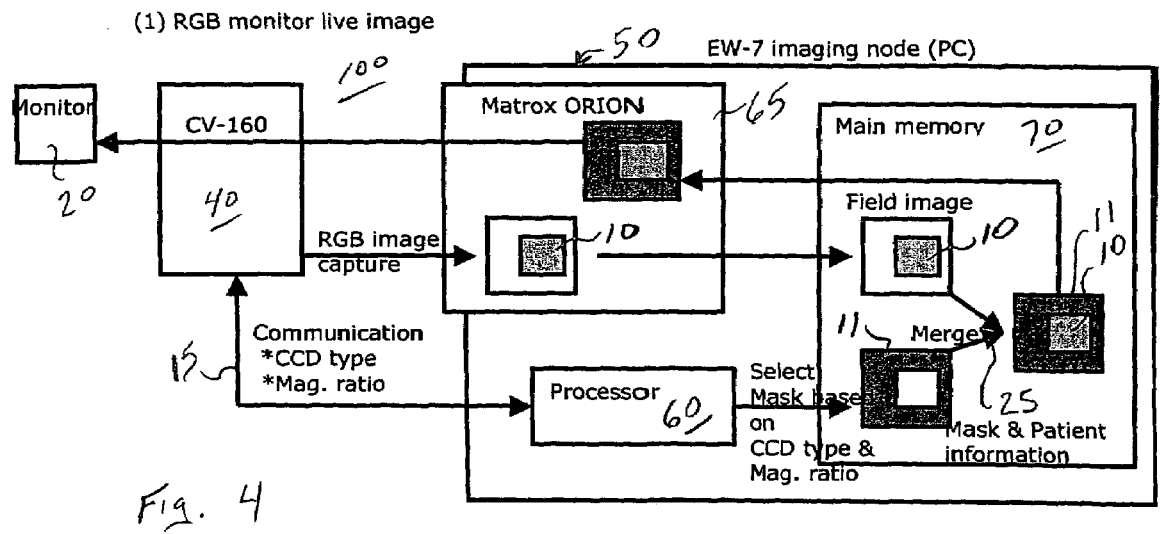
FIGS. 4 and 5 illustrate respective detailed block diagrams of the imaging node processing 50 for supporting two identical, real-time visual displays of the entire endoscopic examination, a first display on the RGB monitor 20 (FIG. 4) and a secondary VGA display 55 (FIG. 5) displayed in an Windows ActiveX component.
Figure 5:
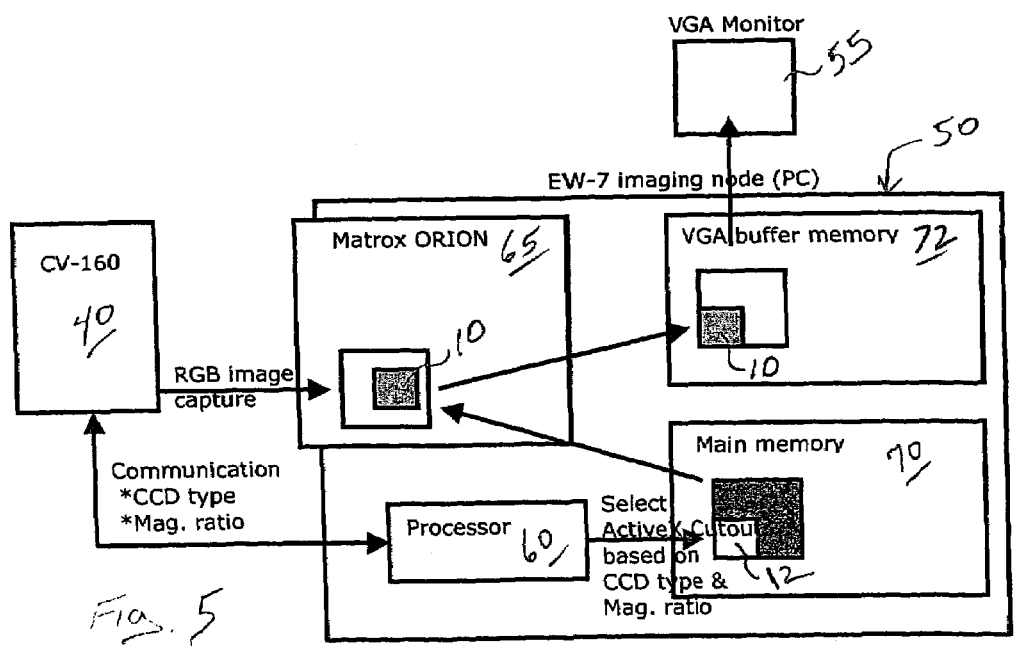

As further shown in a more detailed block diagrams of the EW system 100 depicted in FIGS. 4 and 5, the video display driver element 65 provided in the imaging node 50 supports two identical, real-time visual displays of the entire endoscopic examination. As shown in FIG. 4, the RGB monitor 20 is the primary visual output for medical personnel involved in the examination. As shown in FIG. 5, the secondary display, output to a VGA display 55, is displayed in a Windows "ActiveX" component. The imaging node processor 60 drives both the RGB monitor display 20 as well as the VGA display 55, through the driver element of the Matrox Orion image (frame) capture board 65 in the imaging workstation or PC 50. Integral to the embodiments shown in FIGS. 4-5, is the automatic recognition of the CCD type and a selected magnification ratio. That is, communication between the imaging node 50 and the video processor device 40 is provided, whereby processing in the node interrogates the video processor to determine the type of scope or video chip being used. For example, according to one embodiment, the EW imaging node 50 software will obtain the Scope Chip information associated with endoscope device via communication with the video processor including the Model, Serial number, Scope ID, Channel size, and repair information. It is understood that the CCD type information along with the selected magnification ratio selected is sufficient to display the appropriate mask setting.

According to the present invention, the automated mask feature is provided for the EW system 100 that automatically selects the appropriate video mask based on the endoscope device 25 being used. Corresponding to the system 100 shown for providing the primary visual output of the endoscopic examination, and described with respect to FIG. 4, the operation of the auto-mask feature for presenting real-time live images to the RGB monitor 20 according to the present invention is now described in greater detail. As shown in FIG. 4, the Matrox video grabber device 65 captures live video signal RGB image field 10 from the video processor 40 and sends the captured image field 10 to the main memory 70 of the imaging node 50. The imaging node 50 is programmed to communicate with the video processor 40 via a communications interface 15 to obtain information including the CCD type used in the current endoscopic examination and the magnifying ratio selected, e.g., (medium, semi-full height or full height). The imaging node processor 60 receives this information and selects a pre-determined mask (e.g., a mask 11) based on the CCD type and magnifying ratio selected, and generates the mask pattern in the main memory. As mentioned, the video mask 11 is primarily set up to allow one or more portions of the screen to be viewed while the balance is hidden. Finally, the imaging node 50 performs processing to effectively merge the field image 10 and the mask 11 and transfer the merged mask and field image to the capture board 65 frame memory where the RGB video signal is generated based on the data from frame memory. The generated RGB signal is provided to the RGB monitor 20 through the video processor 40. As will be described, during the merge process, additional data such as patient demographics and scope information 25 are additionally overlayed in specified portions of the mask, e.g., in proximity to the viewable area where the captured still image or live video clip is merged. In accordance with further processing, when initiated by the user, the EW application grab frame function further initiates function to capture a desired image, store the static image, compress the static image, and generate a thumbnail version which is temporarily stored in the imaging node memory, and processed for display via both the RGB and VGA monitors.

With respect to frame grabbing, a coding technique is employed that involves using two asynchronous grab buffers, with the logic calling a user-written "hook" function after it grabs each field of the two-field image frame into a buffer (not shown). While fields of one buffer are being filled, the hook function is simultaneously processing the contents of the other buffer. This alternating technique has the effect of maximizing throughput. Within the hook function, an overlay buffer, that includes the patient information as described herein, is merged with the image grab buffer using the Windows 'Blt' function. This combined buffer is then merged with an image buffer (not shown) associated with the RGB display using an analogous function.

More particularly, upon initialization of the imaging node, the executing software will initiate a search for an automask definition to initialize a video buffer based on the information including the CCD type used in a current endoscopic examination and a magnifying ratio. Otherwise, a default mask, e.g., a "primary" mask, for the node shall be used to initialize the video buffer. Based on the video configuration settings used, the video buffer will be initialized with input signal as RGB or as a composite image. If during the course of an examination, the user selects a different magnification ratio, the executing software will initiate a search for an automask definition to change the mask setting feature in the imaging node based on the CCD type and magnifying ratio selected.

FIG. 6 illustrates an exemplary the RGB monitor display 20 comprising several mask "cutouts" including: a cutout 76 for displaying the animated, real-time endoscopic image; a cutout 77 for displaying Patient information, e.g., with three (3) lines of information giving patient name, patient id, and exam type given; a cutout 78 for displaying a scaled thumbnail version of a selected, previously captured static image. Further shown in display 20 is an image number 75 which is a sequence position of a particular image in a static image capture sequence, and, a record indicator which displays the text string "Record" when a 'Live Video Capture' is selected by a scope head button configured for this purpose as will be described in greater detail. A further indication provided is timer indication that displays the text string "Timer" when a scope button configured to initiate the calculation of scope-in duration is pressed. Although not shown, a further Video Status indication is provided, e.g., exemplified by a word such as "Freeze" when the video image is frozen by scope head control. The primary cutout, in terms of both significance and size, remains the live video display. The user may toggle through different visual cutout "masks", as alternate scope equipment is employed in the examination, with each selection having its own rectangular definitions for the above cutouts. The RGB display is updated instantly with each new mask selection.

As mentioned, a simultaneous display of the imaging activity displayed on the RGB monitor is also shown in a window within an ActiveX component of the EW system application. This display does not contain any other mask information, however; it shows only the live captured images. Thus, as shown and described with respect to FIG. 3, the operation of the auto-mask feature for presenting real-time live images to the secondary display, e.g., VGA monitor 55 according to the present invention is now described in greater detail with respect to FIG. 5. As shown in FIG. 5, the imaging node 50 implements a "pseudo-live" grab function provided with the Matrox video grabber device 65. With this function, the Matrox board writes the captured RGB image 10 from the video processor 40 and sends the captured image field image 10 to a VGA buffer memory 72 based on an ActiveX setting. As in the video mask processing, an ActiveX window object having a cutout area 12 that defines the output view of an ActiveX window 12 is further generated in main memory 70 that defines where, in the mask, the endoscope image is placed in the VGA monitor screen. That is, the application constructs the captured image screen and places the object on the window screen. Like the mask selected for the RGB output display, the ActiveX cutout definition is additionally based on the CCD type and magnifying ratio selected by the user.

FIG. 7 illustrates an exemplary the ActiveX control and VGA display generated according to the present invention.

As shown, the VGA display 80 includes a scaled version of the RGB display, with aspect ratio preserved. A Current Mask setting description 82 associates the set of rectangular coordinates currently in use to define the borders of the real-time image, seen both on the RGB and VGA, plus other informational cutouts displayed only on the corresponding RGB monitor display; a Static Capture button 84 that, when selected, performs a synchronous grab the current frame, writes it to imaging node computer hard drive, and displays a thumbnail version of it in the Image Capture strip, as well as in the RGB thumbnail cutout; a Toggle Freeze/Unfreeze button 86 that, when selected, suspends the live display on both the RGB and VGA for detailed analysis of a single image; a Re-initialize Processor button 88 that, when selected, performs a manual re-initialization of the processor and "MIL" (Matrox Imaging Library) software environment; a Delete Live Clips button 90 that, when selected, enables deletion of one or more recorded video clips. The total time of all recorded video clips for an exam cannot exceed two minutes, for example, although other time durations are acceptable; a Start/Stop Live Capture button 92 that, when selected, initiates toggling of the start or stop of live video capture (it automatically stops when two minutes total recorded time limit is reached, for example); a Live Capture Time Left timer indicator 94 is provided that indicates a count of the number of live video recording seconds currently available. Although the video clips available for storage are limited within 2.0 minutes in this description, a skilled artisan will readily recognize that the limitation is variable depending upon the particular hardware environment implemented. A further feature includes the Toggle Mask button 96, that, when selected, provides an alternative to changing masks by selection from the drop-down list. This functionality will switch to an alternate mask choice and requires a secondary mask to have been identified in the application Node Settings via the node setting interface as will be described in greater detail herein. A further indication on the VGA display is the Processor Status indication 98 providing information on the current processor state. As will further be described in greater detail herein, the Live Capture, Static Capture, Freeze, and Toggle Mask functions may also be invoked from the endoscope device head (or possibly foot switch), depending on hardware capabilities and the user configuration settings on the imaging node settings. Additionally available via scope head controls, when configured within the application, is a 'Toggle Timer' function, which calculates scope-in time duration.

It is understood that, the VGA image frame grabs are "continuous, pseudo-live" grabs, in the MIL parlance. They occur using the hardware capabilities of the Matrox Orion PC board directly to the image buffer 72 associated with the VGA display (FIG. 5). As mentioned, it is required that the images be scaled to fit into the VGA ActiveX cutout so they are not true "live grabs". Unlike the RGB, VGA image grabs are field-level, not frame level, and no non-imaging cutouts are overlaid on it. Thus, no Windows or MIL "bliting", is involved, making it a much simpler configuration.

Figure 8:
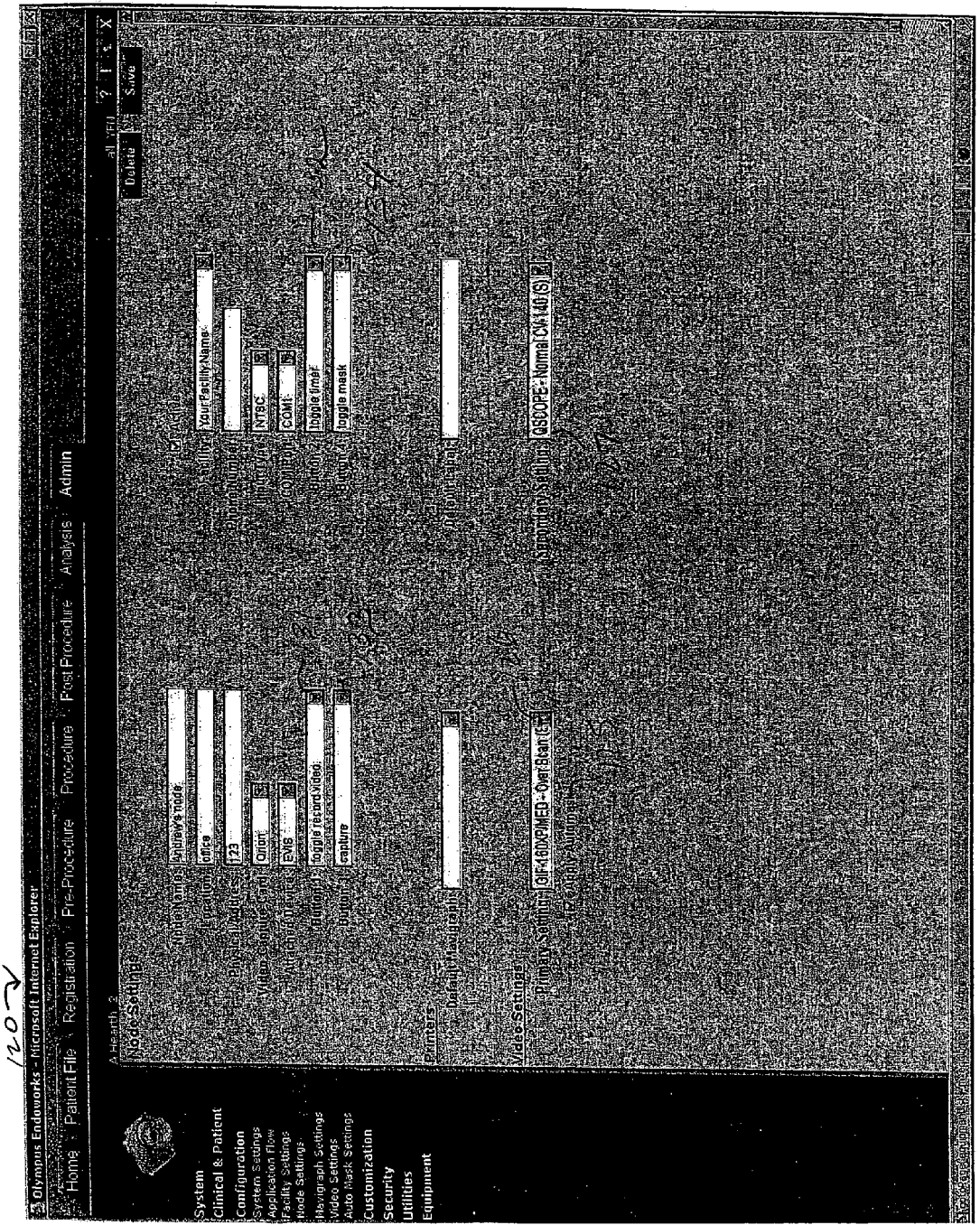
FIG. 8 depicts an exemplary system administration node settings interface 120 that configures the attribute of an individual imaging node, and particularly, the video settings, according to the present invention.

FIG. 8 depicts an exemplary system administration node settings interface 120 that configures the attribute of an individual imaging node, and particularly, the video settings. Particularly, via this settings page 120 the "Automask" setting 125 of the invention is enabled in the EndoWorks system. As further shown, two other system settings are available besides the Automask setting: a primary setting selected via a drop down list 126 of available video settings; and a secondary setting selected via a drop down list 127 where a user can define the video masks for the individual node. Any of the available user or system-defined masks can be chosen. As described herein, a user may manually toggle between Automask, primary and secondary settings. The ability to toggle through these settings allows the user to override the Automask setting or to change input signals to the video capture card. For instance, if a fluoroscopy system that supplies an NTSC composite video signal is used in conjunction with an RGB video processor, the user may manually toggle the video inputs by changing the mask setting depending which image the user would like to view or capture. The user can define the primary or secondary video mask settings for each individual EW imaging node. Any of the available user or system-defined masks can be chosen.

Figure 9:
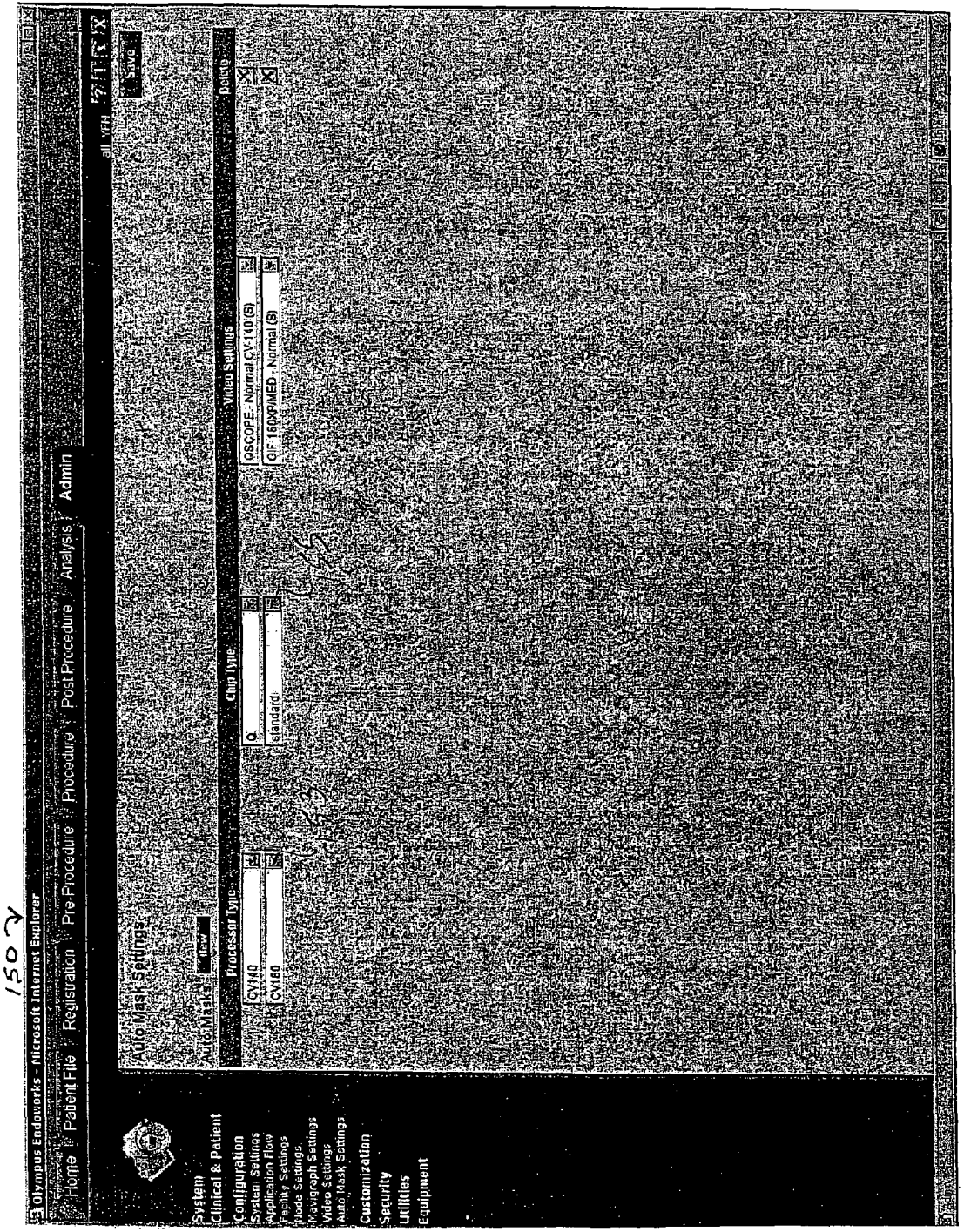
FIG. 9 depicts an exemplary system administration automask setting interface 150 that enables the user to map the combination of video processor and scope video chip to a system or user defined mask according to the present invention.

FIG. 9 depicts an exemplary system administration automask setting interface 150 that enables the user to map the combination of video processor and scope video chip to a system or user defined mask. Particularly, in the EW system, this function is provided essentially to establish the video and automask settings for an imaging node. As shown in FIG. 9, the user may select a video processor type included in the EW system from drop down menu 153 coordinated with a particular endoscope imager (CCD) type 155, e.g., standard, of the scope to be used. A particular video setting 158 that had been previously defined is additionally selected by the user (e.g., a descriptive name) that describes the video configuration, i.e., defines where the locations of the live video, thumbnail and patient information are to be displayed on the monitor, corresponding to the selected processor and chip type. The user selections are mapped to the new automask setting. Thus, as part of imaging node initialization, the default video setting and mask setting is automatically established for user viewing of images on both RGB and VGA monitors that has been established for the particular endoscope, solid-state imager and video setting to be implemented for a particular procedure.

Figures 10A, 10B:
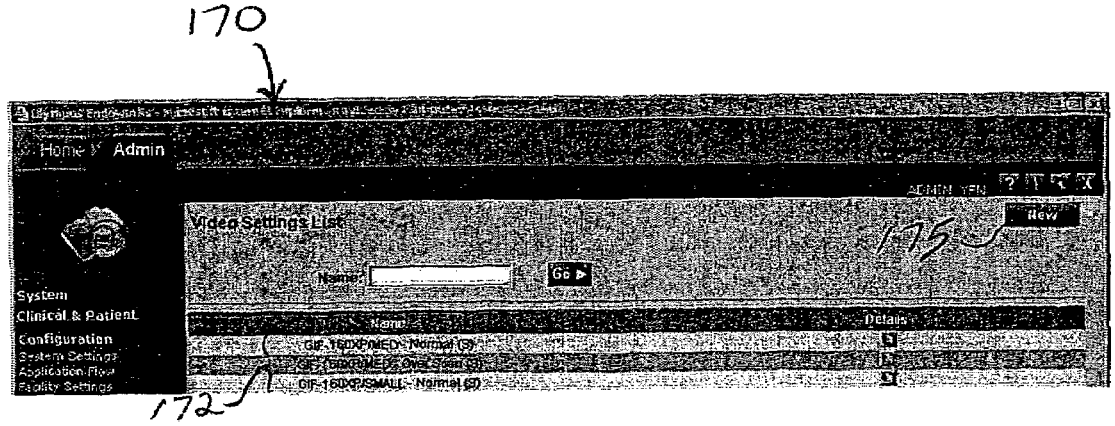
FIG. 10(a) depicts a portion of an exemplary system administration video settings interface 170 that enables a user to add, modify, and delete video configuration settings and, additionally, mask settings, according to the invention.
FIG. 10(b) depicts an exemplary Video Settings interface screen 180 that enables a user to assign mask settings to a new video configuration; and, FIG. 11 depicts an exemplary image capture interface screen 200 providing functionality for enabling image live image capture, selection of the scope information, and tracking scope duration (in/out) times, according to the invention.

FIG. 10(a) depicts a portion of an exemplary system administration video settings interface 170 that enables a user to add, modify, and delete video configuration settings and, additionally, mask settings, which defines how information is displayed on the RGB monitor. To access the video settings list screen 170 the user navigates to the "Admin" tab shown in the figure, and selects the "Configuration" from the menu choices provided at the left side of the screen. Available configuration options are displayed from which the user may select "Video Settings". In response, the Video Settings List screen 170 is displayed which provides the currently defined video settings 172, for instance, sorted alphabetically by name. A user may delete a video configuration (provided it is not associated with an imaging node), however, may not delete or modify application default settings.

To add a new video settings record, the Video Settings List screen of FIG. 10(a) is accessed and the user is prompted to Click the "New" button 175. A Video Settings interface screen 180 is displayed such as shown in FIG. 10(b) that enables a user to assign a name to the new video configuration in the Name field 177, select a source signal from the Video Signal dropdown list 178 and click the Active checkbox 179 to make the configuration-settings available. Further, via Video Settings interface screen 180, the user may define the mask settings 190 by assigning top 192, left 194, bottom 196, and right 198 image frame coordinates settings for each of the live video 183, thumbnail 185, and patient information 188 in the Mask Settings section 190. Then the mask setting for this video configuration is saved and stored in a video setting record such as shown in Table 1. It should be understood that the user is enabled to modify a video settings record by access the Video Settings List screen shown in FIG. 10(*a*), and then selecting the Details icon 177 next to the record that is to be modified. The Video Settings screen is displayed such as shown in FIG. 10(*b*) where the user is able to make the required changes.

The association of imaging node functionality to an endoscope head button is performed via the node settings interface 120 shown in FIG. 8 that illustrates the interface screen within the EW system that further enables the user to establish the configuration of the imaging node settings, including: the node name, location, the node's physical address, the attached endoscope device and the video card implemented in the imaging node (e.g., Matrox ORION), the input video type, a communication port, in addition to the configuration of the primary mask, secondary mask, and, automask function as described herein. Particularly, in the EW system, a system administrative function is provided that enables a user to establish the button settings for the endoscope (the button settings are independent of endoscope type). Thus, as shown

TABLE 1

Column(s) of "video_setting" Table

| Name | Datatype | Null Option | Comment |
|---|---|---|---|
| Ekey | integer | not null | The internal unique identifier for each record in the video_setting table. |
| video_setting_name | varchar(64) | not null | The name given to this video configuration. If the video setting is shipped with the system a (S) will be appended to the name. |
| Shipped | integer1 | not null | Indicates if the video setting configuration is shipped with the system. |
| video_signal | integer | not null | The type of video signal |
| live_video_top | integer | not null | Top coordinate of the live_video frame. |
| live_video_bottom | integer | not null | Bottom coordinate of the live_video frame. |
| live_video_left | integer | not null | Left coordinate of the live_video frame. |
| live_video_right | integer | not null | Right coordinate of the live_video frame. |
| thumbnail_top | integer | not null | Top coordinate of the thumbnail frame. |
| thumbnail_bottom | integer | not null | Bottom coordinate of the thumbnail frame. |
| thumbnail_left | integer | not null | Left coordinate of the thumbnail frame. |
| thumbnail_right | integer | not null | Right coordinate of the thumbnail frame. |
| patient_info_top | integer | not null | Top coordinate of the patient_info frame. |
| patient_info_bottom | integer | not null | Bottom coordinate of the patient_info frame. |
| patient_info_left | integer | not null | Left coordinate of the patient_info frame. |
| patient_info_right | integer | not null | Right coordinate of the patient_info frame. |
| Active | integer1 | not null | Does this record represent an active entity in the Endoworks system? |
| create_date | date | not null | Date and time that this record was created |
| update_date | date | not null | Date and time that this record was last changed |
| endo_user_create_ekey | integer | not null | Foreign key reference to the endo_user who created this record. |
| endo_user_update_ekey | integer | not null | Foreign key reference to the endo_user who last changed this record. |

It is a further aspect of the invention that, the endoscope device itself that is utilized with the EW system during an examination may include programmable function buttons on the device head, for example to enable certain functionality at the EW system imaging node. Thus, the system 100 of FIG. 3 provides a communications link between the EW imaging node computer and the video processor (e.g., CV-160 manufactured and sold by Olympus America, Inc.), such that, the when a button on the scope head is depressed, the video processor will send a signal to the computer indicating which button was depressed. The EW system software will make use of this CV feature by allowing users to associate certain EW system functionality with the button of their choice. The following EW7 system functions may be attributed to buttons on the endoscope device including: 1) a button to initiate image capture functionality including functionality to record live video; 2) toggle exam timer; 3) toggle video mask between the default, primary an secondary video settings; 4) toggle capturing live video; and 5) no function (i.e., the system will use the video processor function as specified).

in FIG. 8, drop down menus are available for each of four (4) buttons provided on the endoscope. In the example interface screen shown in FIG. 8, the button indicated as "Button 1" has been associated with functionality selected from drop-down menu 131 to toggle record video, the button indicated as "Button 2" has been associated with functionality selected from drop-down menu 132 to toggle the timer, the button indicated as "Button 3" has been associated with functionality selected from drop-down menu 133, and, the button indicated as "Button 4" has been associated with functionality selected from drop-down menu 134 to toggle the mask setting. It is understood that, a user, in the course of conducting a procedure, may initiate these functions via the scope itself or, via the VGA ActiveX interface screen, shown and described herein with respect to FIG. 7, rather than from buttons on the scope.

Figure 11:
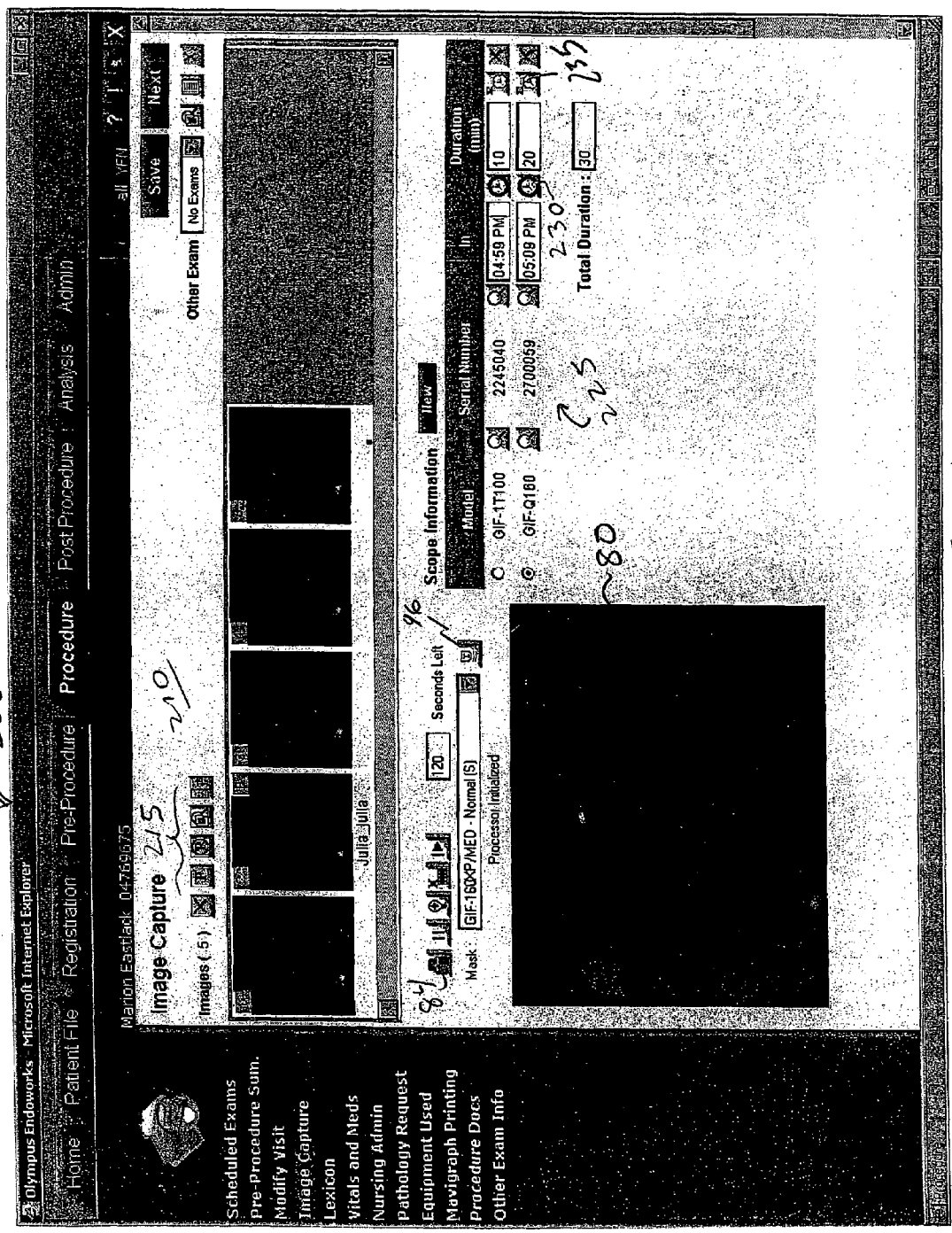

With respect to the toggle Mask function, a user is enabled to toggle between the three video settings (automask, primary, secondary). If the system administrator has applied the automask setting, then a user may either switch between these video settings, or select a new video setting. When a user connects a scope to the system, the default automask settings are applied. Besides implementing EW system functionality from a button located at the scope head, a user is enabled to initiate the functionality from the image capture screen 200 shown herein with respect to FIG. 11. That is, as shown in FIG. 11, via the image capture interface 200, the user is enabled to toggle between the automask settings by selecting the Toggle Mask button 96 located next to the Mask dropdown list as described herein with respect to FIG. 7. The automask settings change to the primary settings. If the user clicks the Toggle Mask button an additional time, the primary settings change to the secondary settings. A further click will change the automask setting back to the default automask settings.

With respect to the image capture functionality of the EW system, during an endoscopic procedure, a user is enabled to capture images and record video clips. The user is further enabled to modify and delete images, and incorporate them into a report document. FIG. 11 illustrates an example image capture interface screen 200 provided on the VGA monitor according to the present invention that includes the live video image 80 provided via the ActiveX control (FIG. 7) and further includes an Image Capture screen portion 210 providing image capture functionality. Icons 215 appearing in the Image Capture screen of FIG. 11 are used to initiate image capture functionality and modify images including: deleting selected images from the current exam; mark selected image(s) for printing and associating clinical report; Unmark the selected image for printing; view a larger image; or show or hide a menu. To access the Image Capture screen, a user navigates to the Procedure tab, selects an exam, and selects Capture Image function from the menu choice shown on the left side of the screen. Particularly, to freeze and capture images, the static capture icon 84 may be clicked (selected) by the user as described with respect to FIG. 7. The captured image(s) 220 is(are) displayed in the Images capture screen portion 210 in sequence, and subsequently stored, deleted, or printed at the discretion of the user. It should be understood that a similar sequence of events is available for recordation of video clips.

As further shown in the image capture interface screen 200 of FIG. 11, a Scope Information section 225 is displayed providing functionality for enabling selection of the Scope Information, for example, when a type of scope is changed during a procedure. The scope information is further associated with the stored images and any corresponding report and patient record generated and stored within the EW system. The user is additionally able to select a Search mode by selecting an icon so enable the user to locate from a dropdown list the particular scope needed to be added. A Scope Model List screen is displayed (not shown). Via a Search icon (listed under the serial number) a model number is selected in addition to a serial number. For a particular procedure, a user is enabled to select the Time icon 230 and select the current time or, alternatively enter it manually. By clicking on the Calculate Duration icon 235, the system calculates the duration of scope use for the procedure, and further enables calculation of the Total Duration time that the scope has been used.

Figure 1:
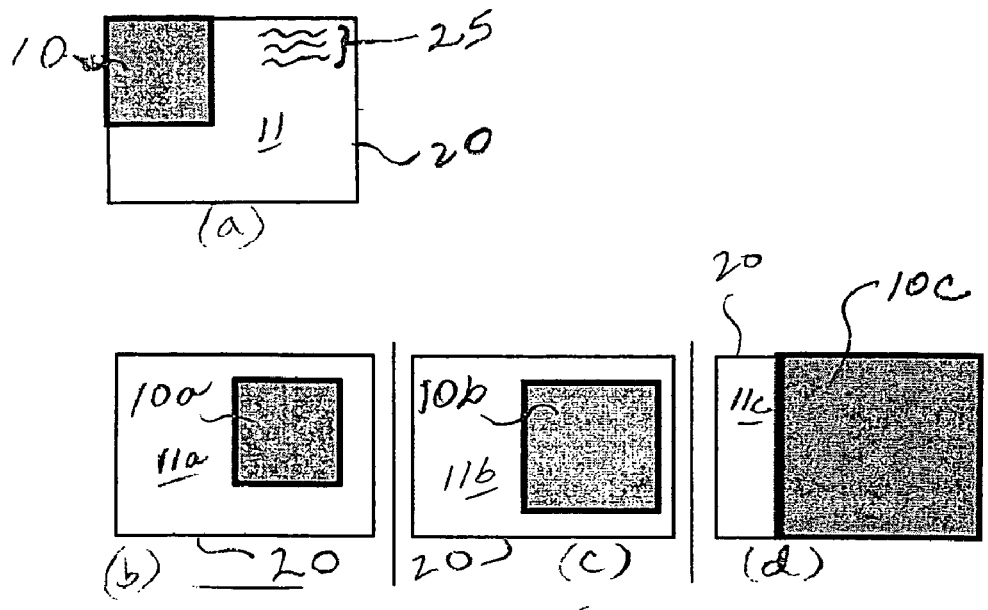
FIGS. 1(a)-1(d) illustrate example displayed live endoscopic image fields on an RGB-type monitor screen 20 for a particular scope CCD imager type and a selected magnification ratio for that scope CCD type according to the prior art.

In a preferred embodiment, the EW system enables the user to program the system to automatically collect Scope In and Out Times. That is, upon automatic recognition and identification of a scope being used for a procedure, timestamps for the scope representing in and out time are automatically captured. The system also enables the user to collect Scope In and Out Times manually by pressing a button on the scope that is allocated "toggle timer" on the node setting screen as shown in FIG. 8. This is especially useful when user exchange scopes during a procedure. For instance as shown in the FIG. 1, two scope models are shown as having been used during a particular procedure such that a first had been used for 10 minutes and a second has been used for a total of 20 minutes for a total duration of 30 minutes, for example.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

Having thus described our invention, what I claim as new, and desire to secure by Letters Patent is:

1. An endoscopic imaging system for performing endoscopic examination of patients, said system comprising a video processor adapted for receiving images from an endoscope device having an imaging device for generating images of an object during an endoscopic examination, said video processor for processing the images into original image signals suitable for display on a first display device, said system comprising:

means for automatically discriminating use of a particular imaging device used during said endoscopic examination;

means operating in cooperation with said video processor device for enabling specification of a magnification ratio for modifying a displayed image;

an imaging node in communication with said video processor adapted to receive said original image signals during the course of an endoscopic examination, capture said original image signals and store captured images in an associated memory device, said imaging node including means for automatically receiving first information representing the imaging device utilized during said examination and for receiving second information representing a specified magnification ratio; and, processing means responsive to said received first and second information for automatically selecting one mask setting from a plurality of stored pre-determined mask settings and, for configuring the selected mask setting in said memory device, said mask setting defining a video image portion to be captured from said original image signals for display on said first display device, wherein said captured video image portion is displayed at a pre-determined portion of said first display device in accordance with said mask setting.

2. The endoscopie imaging system as claimed in claim 1, wherein said first display device displays a live video image or a captured still image portions from said original imaging signals according to said mask setting.

3. The endoscopic imaging system as claimed in claim 2, further comprising: a second display device associated with said imaging node and adapted to display said captured video image area from said original imaging signals.

4. The endoscopic imaging system as claimed in claim 2, wherein said processor means of said imaging node further generates and stores a thumbnail image corresponding to said captured video image portion in response to an applied mask, said mask setting further specifying a thumbnail image display area for displaying said thumbnail image on a defined area of said first display device.

5. The endoscopie imaging system as claimed in claim 2, wherein said mask setting specifies a pre-defined portion of said second display device for displaying said captured video image portion from said original imaging signals.

6. The endoscopic imaging system as claimed in claim 5, wherein said processor means of said imaging node further generates and stores a thumbnail image corresponding to said captured video image portion in response to an applied mask, said processor means of said imaging node enabling display of said generated thumbnail image in a pre-defined area of said second display device.

7. The endoscopic imaging system as claimed in claim 5, further including:
   a means for configuring said system with one or more mask settings based on a video processor and a scope imaging device type; and,
   a mask switching means enabling toggling between different mask settings to be applied to captured images, said switching means further enabling a user to switch between a displayed live video image or a captured still image portion, a thumbnail image, or no image.

8. The endoscopic imaging system as claimed in claim 1, wherein the imaging device includes a solid state CCD imager means for generating real-time frame image signals for processing by said video processor device to generate said original image signals.

9. The endoscopic imaging system as claimed in claim 2, wherein the imaging node comprises a video capture board adapted to capture said original image signals during the course of an endoscopic procedure, said mask setting being applied to a captured image such that only a masked area of said image is stored in said memory.

10. The endoscopic imaging system as claimed in claim 4, wherein said imaging node further comprises switching means for enabling display of endoscopic images or other image signals from an external source.

11. The endoscopic imaging system as claimed in claim 10, wherein said external source includes fluoroscopy equipment or ultrasound equipment for providing respective fluoroscopic or ultrasonic images.

12. The endoscopic imaging system as claimed in claim 3, further comprising:
   a means for tracking and recording information regarding operating use of particular endoscope devices; and,
   a means for enabling switching of mask settings based on said operating use information.

13. An endoscopic imaging apparatus comprising:
   a video processor device adapted for receiving images from an endoscope device having an imaging device for generating images of an object during an endoscopic examination, said video processor for processing the images into original image signals;
   a means for automatically discriminating use of a particular imaging device used during said endoscopic examination;
   a means operating in cooperation with said video processor device for enabling specification of a magnification ratio for modifying a displayed image;
   a processor means in communication with said video processor device for automatically receiving first information representing the imaging device utilized during said examination and for receiving second information representing a specified magnification ratio, said processing means responsive to said received first and second information for automatically selecting one mask setting from a plurality of stored pre-determined mask settings and, for configuring the selected mask setting in a memory device, said mask setting defining a video image portion to be captured from said original image signals for display on said display monitor,
   wherein said captured video image portion is displayed at a predetermined location on a display monitor.

14. The endoscopic apparatus as claimed in claim 13, wherein said captured video image portion is displayed at a location on said display monitor defined according to said mask setting.

15. The endoscopic apparatus as claimed in claim 14, wherein said pre-determined portion of said display screen defined by said mask setting includes a specified object component.

16. The endoscopic apparatus as claimed in claim 14, wherein more than one endoscopic device is utilized during the course of a particular procedure, said apparatus further comprising means for tracking operating use information including a total time duration of use of said one or more scopes.

17. The endoscopic apparatus as claimed in claim 16, further comprising a means for enabling switching of mask settings based on said operating use information.

18. A method for automatically configuring a display in an endoscopic system having an imaging workstation comprising the steps of:
   a) providing an endoscope device including an imaging device for generating images of an object examined during said endoscopic examination;
   b) converting said object images into original image signals suitable for display on a display device;
   c) automatically receiving information regarding said imaging device;
   d) automatically receiving information regarding a specified magnification ratio used for modifying a displayed image;
   e) automatically selecting one mask setting from a plurality of stored pre-determined mask settings and, for configuring the selected mask setting in a memory according to said received endoscope imaging device information and magnification ratio information, said mask setting defining a video image portion to be captured from said original image signals for display; and,
   f) displaying live video or captured images from said endoscope in a pre-defined portion of a display device associated with said workstation.

19. The method for automatically configuring a display as claimed in claim 18, wherein said live video or captured images from said endoscope are displayed in a defined portion of said display device as specified by said mask setting.

20. The method for automatically configuring a display as claimed in claim 18, further including the step of: generating and storing a thumbnail image corresponding to said captured video image portion in response to an applied mask, said mask setting further defining a thumbnail image display area for displaying said thumbnail image on a specified area of said display device.

21. The method for automatically configuring a display as claimed in claim 18, further including the steps of: generating and storing a thumbnail image corresponding to said captured video image portion in response to an applied mask; and, enabling display of said generated thumbnail image in a pre-defined area of said display device.

22. The method for automatically configuring a display as claimed in claim 21, further comprising the steps of:
   configuring said imaging workstation with one or more mask settings based on a video processor and a scope imaging device type; and, enabling toggling between different mask settings to be applied to captured images.

23. The method for automatically configuring a display as claimed in claim 22, further comprising the step of enabling a user to switch between a displayed live video image or a captured still image portion, a thumbnail image, or no image on said display device.

24. The method for automatically configuring a display as claimed in claim 18, further comprising the steps of:
enabling receipt of other image information comprising other image signals from an external source; and,
switching between display of captured endoscopic images and said other image signals from said external source.

25. The method for automatically configuring a display as claimed in claim 24, wherein said external source includes fluoroscopy equipment or ultrasound equipment for providing respective fluoroscopic or ultrasonic images.

26. The method for automatically configuring a display as claimed in claim 18, further comprising the steps of:
tracking and recording information regarding operating use of particular endoscope devices; and,
enabling switching of mask settings based on said operating use information.

* * * * *